United States Patent
Jun (10) Patent No.: US 10,160,456 B2
(45) Date of Patent: Dec. 25, 2018

(54) APPARATUS AND METHOD FOR CONTROLLING VEHICLE BASED ON DEGREE OF FATIGUE

(71) Applicants: HYUNDAI MOTOR COMPANY, Seoul (KR); KIA MOTORS CORPORATION, Seoul (KR)

(72) Inventor: Sung Hwan Jun, Hwaseong-si (KR)

(73) Assignees: Hyundai Motor Company, Seoul (KR); Kia Motors Company, Seoul (KR)

(*) Notice: Subject to any disclaimer, the term of this patent is extended or adjusted under 35 U.S.C. 154(b) by 0 days.

(21) Appl. No.: 15/804,808

(22) Filed: Nov. 6, 2017

(65) Prior Publication Data
US 2018/0297603 A1 Oct. 18, 2018

(30) Foreign Application Priority Data
Apr. 14, 2017 (KR) .................. 10-2017-0048580

(51) Int. Cl.
*B60W 40/08* (2012.01)
*A61B 5/18* (2006.01)
(Continued)

(52) U.S. Cl.
CPC .......... *B60W 40/08* (2013.01); *A61B 5/0205* (2013.01); *A61B 5/0402* (2013.01);
(Continued)

(58) Field of Classification Search
CPC ........ B60W 40/08; B60W 2040/0827; B60W 2040/0872; B60W 2540/26;
(Continued)

(56) References Cited

U.S. PATENT DOCUMENTS 8,022,831 B1* 9/2011 Wood-Eyre ............... B60T 7/14
180/272
2007/0043491 A1* 2/2007 Goerick ............... B60K 28/165
701/41
(Continued)

FOREIGN PATENT DOCUMENTS

JP 2008-036354 A 2/2008
KR 10-2010-0048279 A 5/2010
(Continued)

OTHER PUBLICATIONS

Lee, Jae-Yeol, "A Driver's Drowsiness Detection System Using Biosignal (ECG) of Driver," *Department of Electronics and Display Engineering*, The Graduate School, Catholic University of Daegu, 116 pages.
(Continued)

*Primary Examiner* — Marthe Y Marc-Coleman
(74) *Attorney, Agent, or Firm* — Brinks Gilson & Lione (57) ABSTRACT

An apparatus and a method for controlling a vehicle based on a degree of fatigue of a driver is provided. The apparatus includes: a fatigue degree learning device configured to learn a degree of initial fatigue of the driver based on biometric information of the driver received from a sensor; a fatigue degree monitoring device configured to, when learning the degree of initial fatigue of the driver is completed and driving of a vehicle is started, monitor the degree of fatigue of the driver by receiving the biometric information of the driver from the sensor, and output a control signal corresponding to the degree of fatigue of the driver, and a driving controller configured to control the driving of the vehicle based on the control signal.

17 Claims, 8 Drawing Sheets

(51) Int. Cl.
  *A61B 5/00*      (2006.01)
  *A61B 5/0205*    (2006.01)
  *A61B 5/0402*    (2006.01)
  *A61B 5/0476*    (2006.01)
  *A61B 5/0488*    (2006.01)
  *G05D 1/00*      (2006.01)
  *G08G 1/16*      (2006.01)
  *A61B 5/024*     (2006.01)

(52) U.S. Cl.
  CPC .......... *A61B 5/0476* (2013.01); *A61B 5/0488* (2013.01); *A61B 5/18* (2013.01); *A61B 5/6893* (2013.01); *A61B 5/746* (2013.01); *G05D 1/0061* (2013.01); *G08G 1/167* (2013.01); *A61B 5/024* (2013.01); *A61B 5/02405* (2013.01); *B60W 2040/0827* (2013.01); *B60W 2040/0872* (2013.01); *B60W 2540/26* (2013.01); *B60W 2710/0605* (2013.01); *B60W 2750/308* (2013.01)

(58) Field of Classification Search
  CPC .... B60W 2710/0605; B60W 2750/308; A61B 5/0205; A61B 5/0402; A61B 5/0476; A61B 5/0488; A61B 5/18; A61B 5/6893; A61B 5/746; A61B 5/024; A61B 5/02405; G05D 1/0061; G08G 1/167
  USPC ........ 701/23, 44, 41; 340/576, 575; 180/272
  See application file for complete search history.

(56) References Cited

U.S. PATENT DOCUMENTS

| | | | |
|---|---|---|---|
| 2009/0209829 A1* | 8/2009 | Yanagidaira | A61B 5/165 600/301 |
| 2014/0180145 A1 | 6/2014 | Kanai et al. | |
| 2014/0249722 A1* | 9/2014 | Hegemann | G08G 1/16 701/41 |
| 2014/0276090 A1 | 9/2014 | Breed | |
| 2014/0280177 A1* | 9/2014 | Ishii | G06F 17/30598 707/740 |
| 2014/0361871 A1 | 12/2014 | Silva et al. | |
| 2015/0158425 A1 | 6/2015 | Han et al. | |
| 2015/0164400 A1* | 6/2015 | Shimizu | A61B 5/6893 600/485 |
| 2015/0169834 A1* | 6/2015 | Nishimura | G06Q 10/0639 702/19 |
| 2015/0327803 A1* | 11/2015 | Fujita | A61B 5/11 340/576 |
| 2016/0001781 A1 | 1/2016 | Fung et al. | |
| 2016/0023662 A1* | 1/2016 | Wulf | B60W 40/08 340/576 |
| 2017/0351812 A1* | 12/2017 | Green | B60W 40/09 |

FOREIGN PATENT DOCUMENTS

| | | |
|---|---|---|
| KR | 10-2013-0110820 A | 10/2013 |
| KR | 10-2013-0130538 A | 12/2013 |
| KR | 10-1619271 B | 5/2016 |

OTHER PUBLICATIONS

Sang-Wook Song, Jin-Hee Shin and Thomas Findley, "Relationship Between Fatigue Severity and Heart Rate Variability in Middle-Aged Male Workers," *Korean Journal of Occupational and Environmental Medicine*, 2005, pp. 26-35. http://www.dbpia.co.kr/Article/NODE01155646.

European Search Report for Application No. EP17201278 dated Apr. 23, 2018 (7 pages).

* cited by examiner

| TIME RANGE ANALYSIS INDEX OF HRV | FREQUENCY RANGE ANALYSIS INDEX OF HRVE |
|---|---|
| Mean HRV | VLF |
| SDNN | LF |
| RMS-SD | HF |
| ApEn | LF/HF Ratio |

| WHETHER SCC IS DRIVEN | FATIGUE DEGREE DETECTING STEP | VEHICLE CONTROL |
|---|---|---|
| Off | DETECT FIRST DEGREE OF FATIGUE | PERFORM WARNING ALARM |
| | DETECT SECOND DEGREE OF FATIGUE | MAINTAIN VEHICLE-TO-VEHICLE DISTANCE AND AUTOMATICALLY ACTIVATE LDWS_LKAS |
| On | DETECT FIRST DEGREE OF FATIGUE | PERFORM WARNING ALARM |
| | DETECT SECOND DEGREE OF FATIGUE | NOT PERFORM ACTIVE CONTROL OF VEHICLE |

APPARATUS AND METHOD FOR CONTROLLING VEHICLE BASED ON DEGREE OF FATIGUE

CROSS-REFERENCE TO RELATED APPLICATION

The present application claims priority to and the benefit of Korean Patent Application No. 10-2017-0048580, filed on Apr. 14, 2017, which is incorporated herein by reference in its entirety.

FIELD

The present disclosure relates to an apparatus and a method for controlling a vehicle based on a degree of fatigue.

BACKGROUND

The statements in this section merely provide background information related to the present disclosure and may not constitute prior art.

The traffic accident rate is increasing every year, and dozing off while driving due to an increase of the degrees of fatigue of the drivers accounts for a great part of traffic accidents.

Accordingly, the technologies for measuring the degree of fatigue of the driver while driving and informing his or her degree of fatigue have been developed, and to this end, vehicular sensors for measuring biometric signals, such as an electrocardiogram (ECG), an electroencephalogram (EEG), and an electromyograph (EMG) have been actively developed.

Many studies on electroencephalogram (EEG) sensors for vehicles have been made, and in addition, various technologies for sensing of biometric signals also have been developed.

However, the studies on how the analyses of the degrees of fatigue will be utilized in control of vehicles are not sufficient.

SUMMARY

The present disclosure provides an apparatus and a method for controlling a vehicle based on a degree of fatigue of a driver, which is capable of detecting a degree of fatigue of the driver by utilizing biometric information of the driver and actively controlling the vehicle.

In some forms of the present disclosure, an apparatus for controlling a vehicle based on a degree of fatigue of a driver may include: a fatigue degree learning device configured to learn a degree of initial fatigue of the driver based on biometric information of the driver received from a sensor, a fatigue degree monitoring device that, when learning of the degree of initial fatigue of the driver is completed and driving of a vehicle is started, is configured to monitor the degree of fatigue of the driver based on the biometric information of the driver received from the sensor, and output a control signal corresponding to the degree of fatigue of the driver, and a driving controller configured to control the driving of the vehicle based on the control signal.

The fatigue degree learning device may be configured to learn the degree of initial fatigue of the driver based on the biometric information of the driver received during a preset learning period for the degree of initial fatigue of the driver.

The fatigue degree learning device may be configured to analyze a heart rate variability (HRV) from the biometric information based on a frequency range, and learn the degree of initial fatigue of the driver based on first log values for a low frequency (LF) and a high frequency (HF) during the preset learning period for the degree of initial fatigue of the driver.

The fatigue degree monitoring device may be configured to analyze a heart rate variability (HRV) from the biometric information received during a preset monitoring period for the degree of fatigue of the driver when the vehicle travels by based on the frequency range, and may detect a degree of current fatigue of the driver based on second log values for the LF and the HF during the preset monitoring period for the degree of fatigue of the driver.

The fatigue degree monitoring device may be configured to identify an increment of the degree of fatigue of the driver based on reduction ratios of the second log values for the LF and the HF with reference to the first log values for the LF and the HF.

The fatigue degree monitoring device may be configured to output a first control signal corresponding to a first degree of fatigue when it is identified that the second log values for the LF and the HF decrease by not less than a first reference value and less than a second reference value, and output a second control signal corresponding to a second degree of fatigue when it is identified that the second log values for the LF and the HF decrease by not less than the second reference value.

The driving controller may be configured to output a warning alarm based on the first control signal.

The driving controller may be configured to control a vehicle-to-vehicle distance of the vehicle based on the second control signal.

The driving controller may be configured to interrupt a data of an accelerator position sensor of the vehicle from being transferred to a throttle valve when a distance between the vehicle and a preceding vehicle is less than a preset distance.

The driving controller may be configured to activate a lane departure warning system (LDWS) and a lane keeping assist system (LKAS) based on the second control signal.

The driving controller may be configured to check a setting of a smart cruise control (SCC) system of the vehicle when the fatigue degree monitoring device outputs the control signal fatigue degree monitoring device The driving controller may be configured to control the driving of the vehicle based on the control signal when the smart cruise control (SCC) system is set to be off.

The driving controller may be configured to output a warning alarm based on the control signal when the smart cruise control (SCC) system is set to be on.

The biometric information may include at least one of an electrocardiogram (ECG), an electroencephalogram (EEG), or an electromyograph (EMG).

In other forms of the present disclosure, a method for controlling a vehicle based on a degree of fatigue of a driver may include: learning a degree of initial fatigue of the driver based on biometric information of the driver received from a sensor, when learning the degree of initial fatigue of the driver is completed and driving of a vehicle is started, monitoring the degree of fatigue of the driver based on the biometric information of the driver received from the sensor, outputting a control signal corresponding to the degree of fatigue of the driver, and controlling the driving of the vehicle based on the control signal.

Further areas of applicability will become apparent form the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of examples, reference being made to the accompanying drawings, in which:

FIGS. 2A to 3 are views illustrating a fatigue degree analyzing operation of the apparatus;

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In addition, terms, such as first, second, A, B, (a), (b) or the like may be used herein when describing components of the present disclosure. The terms are provided only to distinguish the elements from other elements, and the essences, sequences, orders, and numbers of the elements are not limited by the terms. In addition, unless defined otherwise, all terms used herein, including technical or scientific terms, have the same meanings as those generally understood by those skilled in the art to which the present disclosure pertains. The terms defined in the generally used dictionaries should be construed as having the meanings that coincide with the meanings of the contexts of the related technologies, and should not be construed as ideal or excessively formal meanings unless clearly defined in the specification of the present disclosure.

Figure 1:
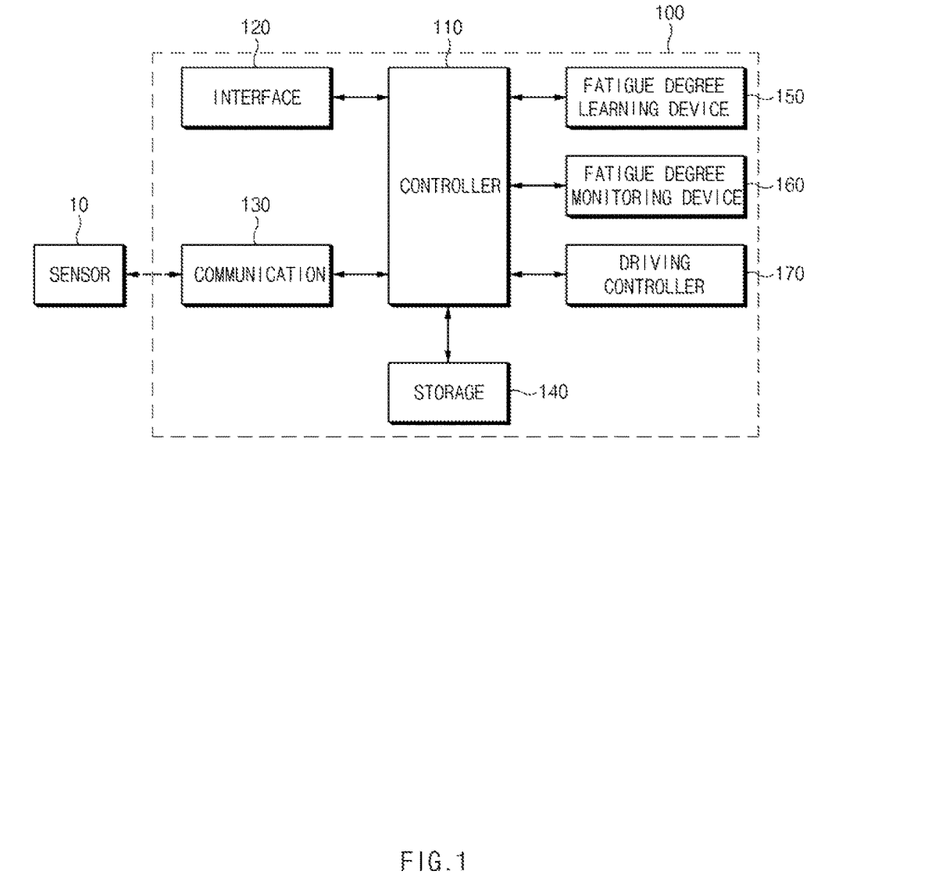
FIG. 1 is a block diagram illustrating a configuration of an apparatus.

FIG. 1 is a block diagram illustrating a configuration of an apparatus in some forms of the present disclosure.

The apparatus 100 may be embodied in the interior of the vehicle. Then, the apparatus 100 may be integrally formed with controllers in the interior of the vehicle, and may be embodied as a separate apparatus to be connected to the controllers of the vehicle by a separate connection unit. Here, the apparatus 100 may be operated in association with biometric signal measuring sensors provided in a seat and a steering wheel of the vehicle. Further, the apparatus 100 may be operated in association with an engine and a motor of the vehicle, and may be operated in association with a controller that controls an operation of the engine or the motor.

Accordingly, referring to FIG. 1, the apparatus 100 may include a controller 110, an interface 120, a communication 130, a storage 140, a fatigue degree learning device 150, a fatigue degree monitoring device 160, and a driving controller 170. Here, the controller 110 may process signals delivered between the elements of the apparatus 100.

The interface 120 may include an input unit that receives a control command from a user, and an output unit that outputs an operation state and a result of the apparatus 100.

Here, the input unit may include a key button, and may include a mouse, a joystick, a jog shuttle, and a stylus pen. Further, the input unit may include a soft key that is embodied on a display.

The output unit may include a display, and may include a voice output unit such as a speaker. Then, when a touch sensor, such as a touch film, a touch sheet, and a touch pad, is provided in the display, the display may be operated as a touch screen, and may be embodied in a form in which an input unit and an output unit are integrated.

Then, the display may include at least one of a liquid crystal display (LCD), a thin film transistor-liquid crystal display (TFT-LCD), an organic light-emitting diode (OLED), a flexible display, a field emission display (ILD), and a 3D display.

The communication 130 may include a communication module that supports a communication interface with electronic components and/or controllers provided in the vehicle. As an example, the communication module may receive a signal transmitted from a sensor 10 provided in the vehicle.

Here, the sensor 10 may include one or more sensors that measure biometric signals of the driver, for example, an electrocardiogram (ECG), an electroencephalogram (EEG), and an electromyograph (EMG). Of course, any other sensor that may measure a fatigue state of the driver may be applied. Although FIG. 1 illustrates that the sensor 10 is realized separately from the apparatus, the sensor 10 may be realized to be included in a vehicle control apparatus in some forms of the present disclosure.

The communication module may store a biometric signal of the driver received from the sensor 10 in the storage 140 or may deliver the biometric signal to the controller 110. Further, the communication module may receive state information of the vehicle, for example, ignition (IG) on/off state information, driving state information, fatigue degree analysis control function setting information, SCC function setting information, lane deviation information, and vehicle-to-vehicle distance information, and may deliver the received state information of the vehicle to the controller 110.

Further, the communication module may transmit a control signal of the driving controller 170 to driving systems of the vehicle, for example, an advanced smart cruise control (ASCC) system and a lane departure warning system (LDWS) and a lane keeping assist system (LKAS).

Here, the communication module may include a module that supports network communication of the vehicle, such as controller area network (CAN) communication, local interconnect network (LIN), or Flex-Ray communication.

Further, the communication module may include a module for wireless internet connection or a module for short range communication. Here, the wireless internet technology may include wireless LAN (WLAN), wireless broadband (WiBro), Wi-Fi, or world interoperability for microwave access (WiMax), and the short range communication technology may include Bluetooth, ZigBee, ultra-wideband (UWB), radio frequency identification (RFID), and infrared data association (IrDA).

The storage 140 may store data and/or algorithms that are necessary for operating the apparatus 100.

The storage 140 may store biometric information of the driver received through the communication 130. Further, the storage 140 may store initial fatigue degree learning information learned by the fatigue degree learning device 150.

Further, the storage 140 may store condition information for allowing the user to actively control the vehicle according to the degree of fatigue of the driver. As an example, the storage 140 may store initial fatigue degree learning time information, a fatigue degree monitoring cycle, a heart rate variability (HRV) analysis index, LF/HF reduction rates for the HRVs for steps of the degrees of fatigue, and the like.

Further, the storage 140 may store a fatigue degree analysis algorithm according to the HRV of the driver, and may store a command and/or algorithm for actively controlling driving of the vehicle according to the degrees of fatigue for steps.

Here, the storage 140 may include storage media, such as a random access memory (RAM), a static random access memory (SRAM), a read-only memory (ROM), a programmable read-only memory (ROM), and an electrically erasable programmable read-only memory.

If it is identified that an ignition-on signal of the vehicle is input while the fatigue degree analysis control function is set to be on in advance, the controller 110 may control an operation of the communication 130 to receive biometric information of the driver, for example, electrocardiogram (ECG) information from the sensor 10. Then, the communication 130 may receive electrocardiogram (ECG) information of the driver for a predetermined initial fatigue degree learning period.

If receiving electrocardiogram (ECG) information through the communication 130, the controller 110 delivers the received electrocardiogram (ECG) information to the fatigue degree learning device 150.

After the ignition of the vehicle is switched on, the fatigue degree learning device 150 learns a degree of initial fatigue by using the electrocardiogram (ECG) information of the driver delivered from the controller 110 during the initial fatigue degree learning period.

The fatigue degree learning device 150 may receive health information of the driver, for example, cardiovascular disease information in advance through the interface 120.

The fatigue degree learning device 150 may analyze a degree of fatigue corresponding to the electrocardiogram (ECG) information of the driver by executing an algorithm for analyzing a degree of fatigue by using the electrocardiogram (ECG) information of the driver.

The fatigue degree learning device 150 analyzes a heart rate variability (HRV) with reference to an R-R interval time of an electrocardiogram (ECG) waveform. Here, a form of an electrocardiogram (ECG) waveform will be described with reference to FIGS. 2A and 2B.

Figure 2A:
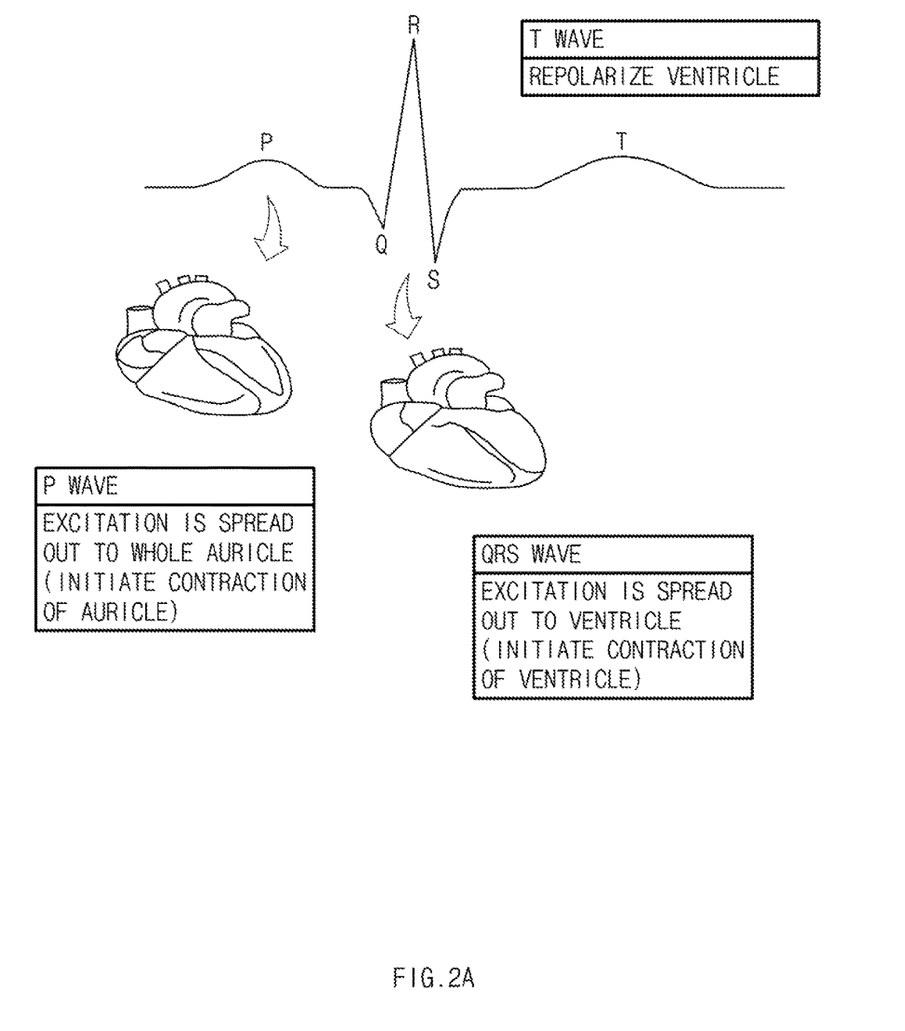
Figure 2B:
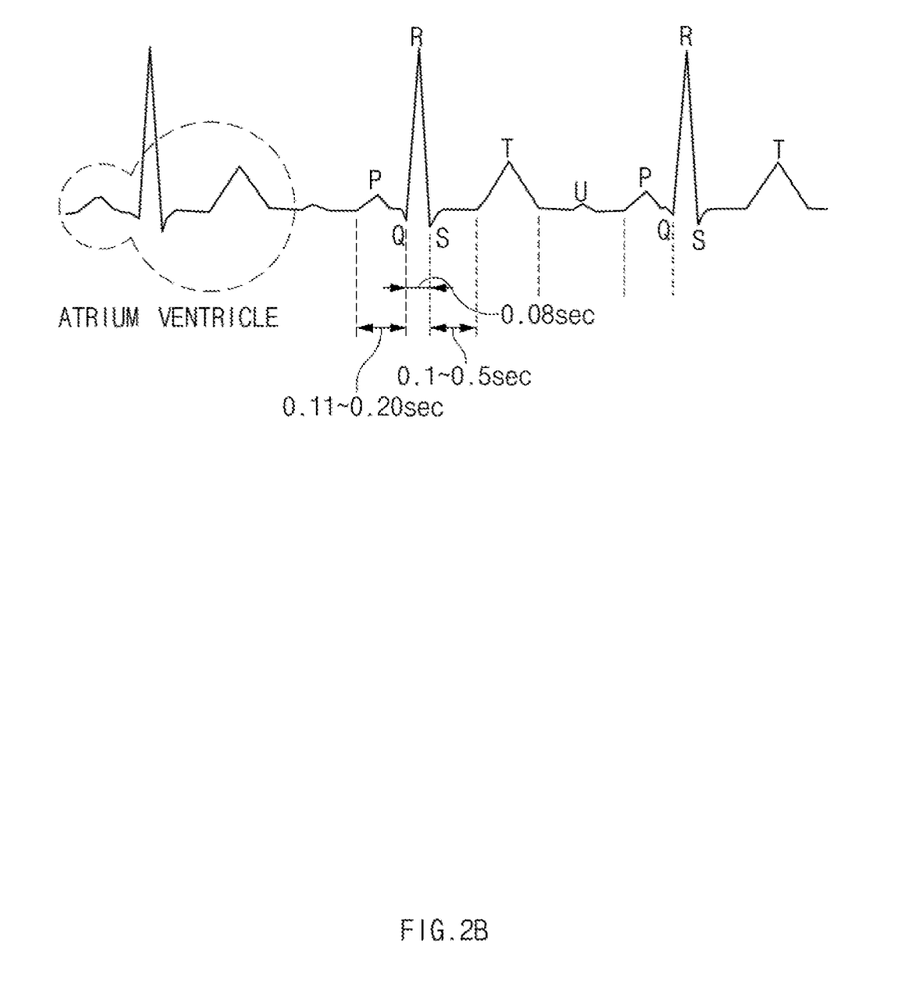

Referring to FIGS. 2A and 2B, an electrocardiogram (ECG) waveform may be classified into a P wave, a QRS wave, and a T wave. The P wave is a waveform generated when an excitation is diffused to the whole cardiac auricle and contraction of the cardiac auricle is initiated. The QRS wave is a wave formed generated when an excitation is diffused to the whole ventricle and contraction of the ventricle is initiated. Further, a T wave is a side-product waveform generated when an excitation of a ventricle calms down.

The heart rate variability (HRV) is analyzed through a time range analysis and a frequency range analysis. Here, the fatigue degree learning device 150 may learn a degree of initial fatigue of the driver by using an HRV analysis parameter through a frequency range analysis.

Figure 3:
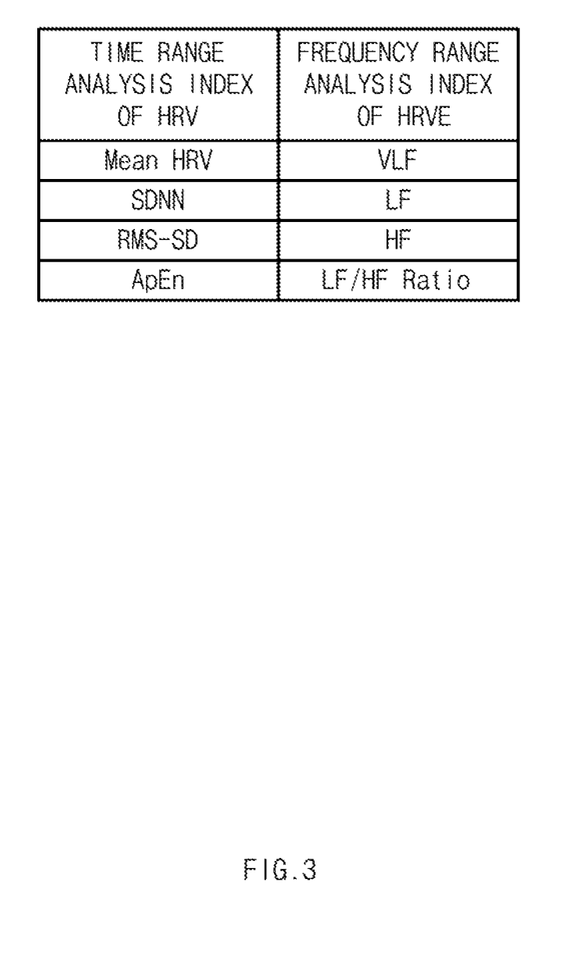

The HRV analysis parameter through the frequency range analysis may be represented as in FIG. 3.

As illustrated in FIG. 3, the HRV analysis parameter through the frequency range analysis may include a very low frequency (VLF), a low frequency (LF), a high frequency (HF), and an LF/HF ratio parameter.

Here, the LF corresponds to a frequency band of 0.04 [Hz] to 0.15 [Hz], and may reflect a sympathetic nervous system and a parasympathetic nervous system. Accordingly, the fatigue degree learning device 150 may determine a degree of physical fatigue, loss of internal energy, lack of sleep, and/or lethargy.

Further, the HF corresponds to a frequency band of 0.15 [Hz] to 0.4 [Hz], and may reflect an activity and a respiration state of a parasympathetic nervous system. Accordingly, the fatigue degree learning device 150 may determine a degree of psychological fatigue, aging, and/or chronic stress according to a change rate of the HF.

Then, the fatigue learning device 150 calculates first log values for the LF and the HF during the initial fatigue degree learning period, and learns a degree of initial fatigue of the driver by using the calculated first log values for the LF and HF. Here, the first log values for the LF and the HF may be average values of the log values calculated during the initial fatigue degree learning period.

In detail, the fatigue degree learning device 150 performs a fast Fourier transform on data based on a time domain by acquiring an R-R interval time of the electrocardiogram (ECG) waveform, and learns a degree of initial fatigue of the driver by calculating average values of ln(LF) values and LN(HF) values during the initial fatigue degree learning period, for example, for 5 minutes.

The initial fatigue degree information of the driver learned by the fatigue degree learning device 150 is stored in the storage 140.

If identifying that the vehicle starts to travel after the degree of initial fatigue of the driver is learned, the controller 110 may control an operation of the communication 130 to receive biometric information, for example, electrocardiogram (ECG) information of the driver from the sensor 10 during driving of the vehicle. Then, the communication 130 may receive electrocardiogram (ECG) information of the driver at a predetermined fatigue degree monitoring cycle. Of course, the communication 130 may receive electrocardiogram (ECG) information of the driver in real time according to a setting state.

If receiving electrocardiogram (ECG) information through the communication 130, the controller 110 delivers the received electrocardiogram (ECG) information to the fatigue degree monitoring device 160.

Like the fatigue degree learning device 150, the fatigue degree monitoring device 160 may analyze a degree of fatigue corresponding to the electrocardiogram (ECG) information of the driver by executing an algorithm for analyzing a degree of fatigue by using the electrocardiogram (ECG) information of the driver.

Because the technology of analyzing a degree of fatigue by using electrocardiogram (ECG) information of the driver has been described above, a detailed description thereof will be omitted.

Then, the fatigue degree monitoring device 160 calculates second log values for the LF and the HF during the fatigue degree monitoring time cycle, and learns a degree of current fatigue of the driver by using the calculated second log values for the LF and HF. Here, the second log values for the LF and the HF may be average values of the log values calculated during the fatigue degree monitoring time cycle.

The ln(LF) value and ln(HF) value calculated by using the electrocardiogram (ECG) information of the driver decrease as the degree of fatigue of the driver increases.

Accordingly, the fatigue degree monitoring device 160 identifies an increment state of the degree of fatigue by comparing fatigue degree information of the driver analyzed through the fatigue degree learning cycle or in real time during driving of the driver and initial fatigue degree information learned by the fatigue degree learning device 150.

Then, the fatigue degree monitoring device 160 identifies ratios at which the ln(LF) values and the ln(HF) values calculated during the fatigue degree learning cycle while the vehicle travels with reference to the average value of the ln(LF) values and the average value of the ln(HF) values, which have been initially learned by the fatigue degree learning device 150 during the initial fatigue degree learning period, are reduced.

Meanwhile, the fatigue degree monitoring device 160 identifies ratios at which the average values of the ln(LF) values and the ln(HF) values calculated in real time while the vehicle travels with reference to the average value of the ln(LF) values and the average value of the ln(HF) values, which have been initially learned by the fatigue degree learning device 150 during the initial fatigue degree learning period, are reduced.

For example, the fatigue degree monitoring device 160 may determine that the degree of fatigue reaches a first degree of fatigue if it is identified that the average values of the ln(LF) values and the ln(HF) values calculated while the vehicle travels with reference to the average value of the ln(LF) values and the average value of the ln(HF) values, which have been initially learned by the fatigue degree learning device 150 during the initial fatigue degree learning period, are reduced by not less than a first reference value (A[%]) and less than a second reference value (B[%]).

The fatigue degree monitoring device 160 outputs a first control signal to the driving controller 170 if it is identified that the degree of fatigue of the driver reaches a first degree of fatigue while the vehicle travels.

Meanwhile, the fatigue degree monitoring device 160 may determine that the degree of fatigue reaches a second degree of fatigue if it is identified that the average values of the ln(LF) values and the ln(HF) values calculated while the vehicle travels with reference to the average value of the ln(LF) values and the average value of the ln(HF) values, which have been initially learned by the fatigue degree learning device 150 during the initial fatigue degree learning period, are reduced by not less than a second reference value (B[%]).

The fatigue degree monitoring device 160 outputs a second control signal to the driving controller 170 if it is identified that the degree of fatigue of the driver reaches a second degree of fatigue while the vehicle travels.

The driving controller 170 outputs a warning alarm through an output unit of the interface 120 if receiving the first control signal from the fatigue degree monitoring device 160. Then, the driving controller 170 may output a warning alarm at a predetermined cycle. Accordingly, an attention of the driver may be called through the warning alarm.

Meanwhile, the driving controller 170 outputs an operation control command for maintaining a vehicle-to-vehicle distance at a specific distance to a driving unit of the vehicle, for example, an accelerator and/or a brake if receiving a second control signal from the fatigue degree monitoring device 160. Further, the driving controller 170 may transmit a command for controlling maintenance a vehicle-to-vehicle distance and maintenance of a lane, through a driving assist system of the vehicle, for example, an advanced smart cruise control (ASCC) system, a lane departure warning system (LDWS), and a lane keeping assist system (LKAS).

Further, the driving controller 170 may allow a data value of an accelerator position sensor to be delivered to a throttle valve only when the vehicle-to-vehicle distance is a preset distance or more, and may interrupt the data value of the accelerator position sensor from being delivered to the throttle valve even though the driver manipulates the accelerator if the vehicle-to-vehicle distance is less than the set distance.

Figure 4:
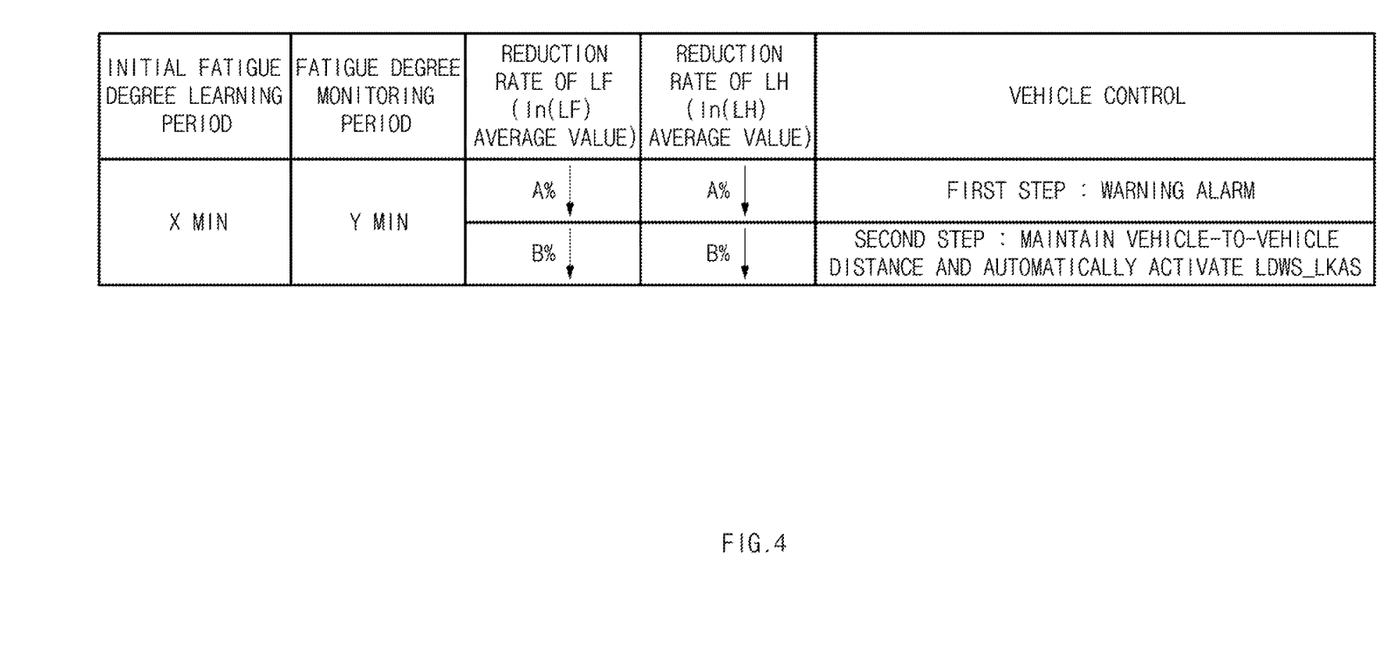
FIGS. 4 to 5 are views illustrating a vehicle controlling operation of the apparatus.

An initial fatigue degree learning period, a fatigue degree monitoring cycle, an LF reduction rate, and an HF reduction rate, and vehicle control information based on them may be defined in a form of a table and may be stored in the storage 140 as illustrated in FIG. 4.

Meanwhile, the driving controller 170 may identify a setting state of the smart cruise control (SCC) system before performing a control corresponding to the first control signal or the second control signal output from the fatigue degree monitoring device 160.

The smart cruise control (SCC) system is a system that performs a function of driving a vehicle at a constant speed when there is no preceding vehicle, performs a function of maintaining a distance from a preceding vehicle when there is the preceding vehicle, and performs a function of driving a vehicle at a constant speed set by the driver when a preceding vehicle disappears.

If the smart cruise control (SCC) system is set to be on, a need to actively control the vehicle according to the degree of fatigue of the driver lowers.

Figure 5:
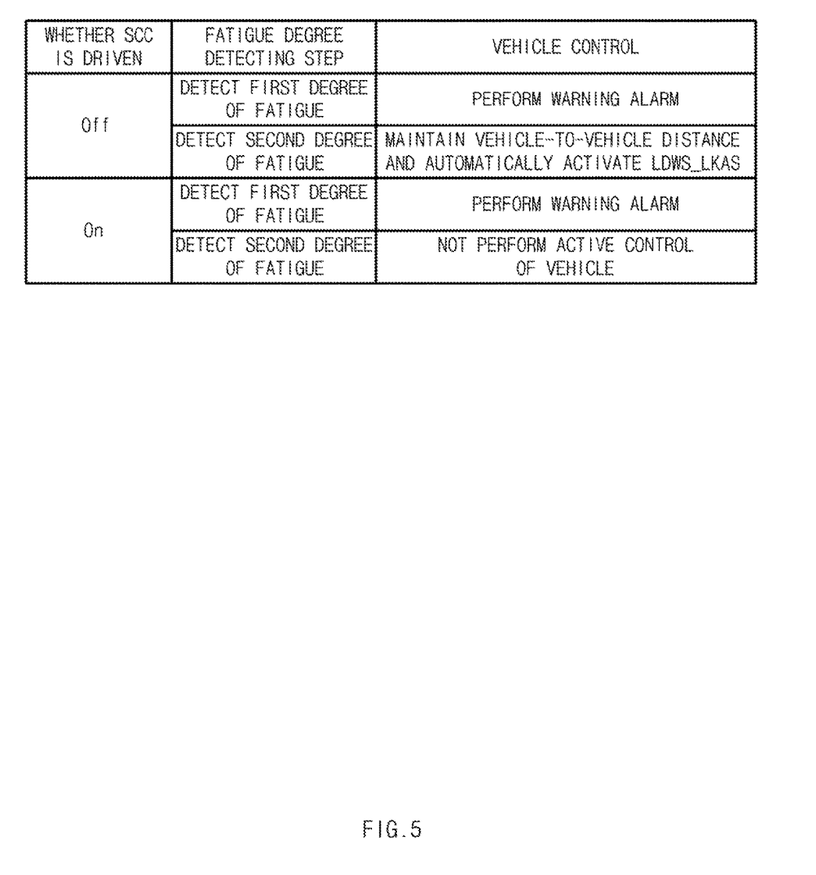

Accordingly, as illustrated in FIG. 5, the driving controller 170 performs a corresponding control operation if the first control signal or the second control signal is output while the smart cruise control (SCC) system is set to be off, whereas the driving controller 170 does not perform an active control operation for maintaining a vehicle-to-vehicle distance when the degree of fatigue reaches a second degree of fatigue if the smart cruise control (SCC) system is set to be on and the second control signal is output from the fatigue degree monitoring device 160.

Meanwhile, the driving controller 170 may allow a warning alarm to be output to call an attention of the driver if the degree of fatigue of the driver increases to the first degree of fatigue and the first control signal is output from the fatigue degree monitoring device 160.

An operational flow of the apparatus according to the present disclosure will be described in detail.

Figure 6:
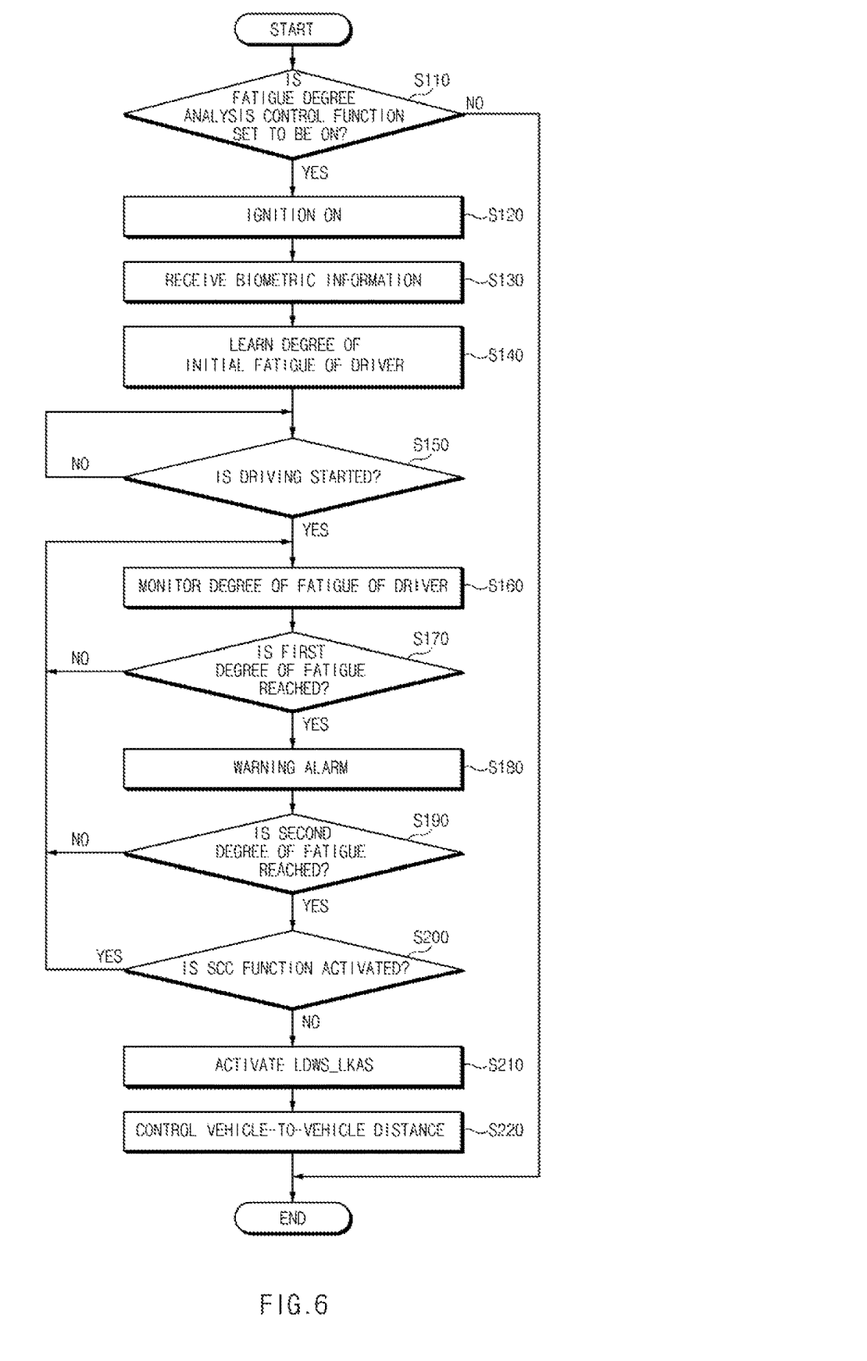
FIG. 6 is a flowchart illustrating an operation a method.

FIG. 6 is a flowchart illustrating an operation a method in some forms of the present disclosure.

Referring to FIG. 6, if an ignition-on signal is input to the vehicle (S120) while a fatigue degree analysis control function is set to be on (S110), the apparatus according to the present disclosure may receive biometric information of the driver, for example, electrocardiogram (ECG) information (S130). Then, the apparatus may receive electrocardiogram (ECG) information of the driver for a predetermined initial fatigue degree learning period.

The apparatus learns a degree of initial fatigue by using the electrocardiogram (ECG) information of the driver received during the initial fatigue degree learning period (S140).

In process S140, the apparatus may analyze a heart rate variability (HRV) with reference to an R-R interval time of an electrocardiogram (ECG) waveform, and may learn a degree of initial fatigue by calculating average values of a ln(LF) value and a ln(HF) value during the initial fatigue degree learning period, respectively.

Thereafter, if the vehicle starts to travel (S150), the apparatus receives biometric information of the driver, for example, electrocardiogram (ECG) information from the sensor 10, and monitors the received electrocardiogram (ECG) information (S160).

In process S160, the apparatus monitors a degree of fatigue of the driver by receiving electrocardiogram (ECG) information of the driver at a monitoring cycle or in real time and identifying reduction ratios of the average values of the ln(LF) values and the ln(HF) values calculated during the fatigue degree learning period while the vehicle travels.

If it is identified after the monitoring of the degree of fatigue of the driver that the degree of fatigue reaches the first degree of fatigue (S170), the apparatus outputs a warning alarm through an output unit of the interface 120 to call an attention of the driver (S180).

Meanwhile, if the average value of the ln(LF) values and the average value of the ln(HF) values calculated while the vehicle travels decrease at a specific ratio or more and the degree of fatigue reaches to the second degree of fatigue (S190), the apparatus identifies whether the smart cruise control (SCC) system function is activated. If the smart cruise control (SCC) system function is not activated in the vehicle (S200), the apparatus activates a lane departure warning system (LDWS) and a lane keeping assist system (LKAS) and performs a control to output a control command to the driving unit of the vehicle, for example, an accelerator and/or a brake and maintain the vehicle-to-vehicle distance at a specific distance (S210). Of course, the advanced smart cruise control (ASCC) system may be activated without the accelerator and/or the brake is not directly controlled.

The apparatus 100 in some forms of the present disclosure may be embodied in a form of an independent hardware apparatus and may be driven in a form in which the apparatus 100 is included in another hardware apparatus such as a microprocessor or a general-purpose computer system, as at least one processor.

Figure 7:
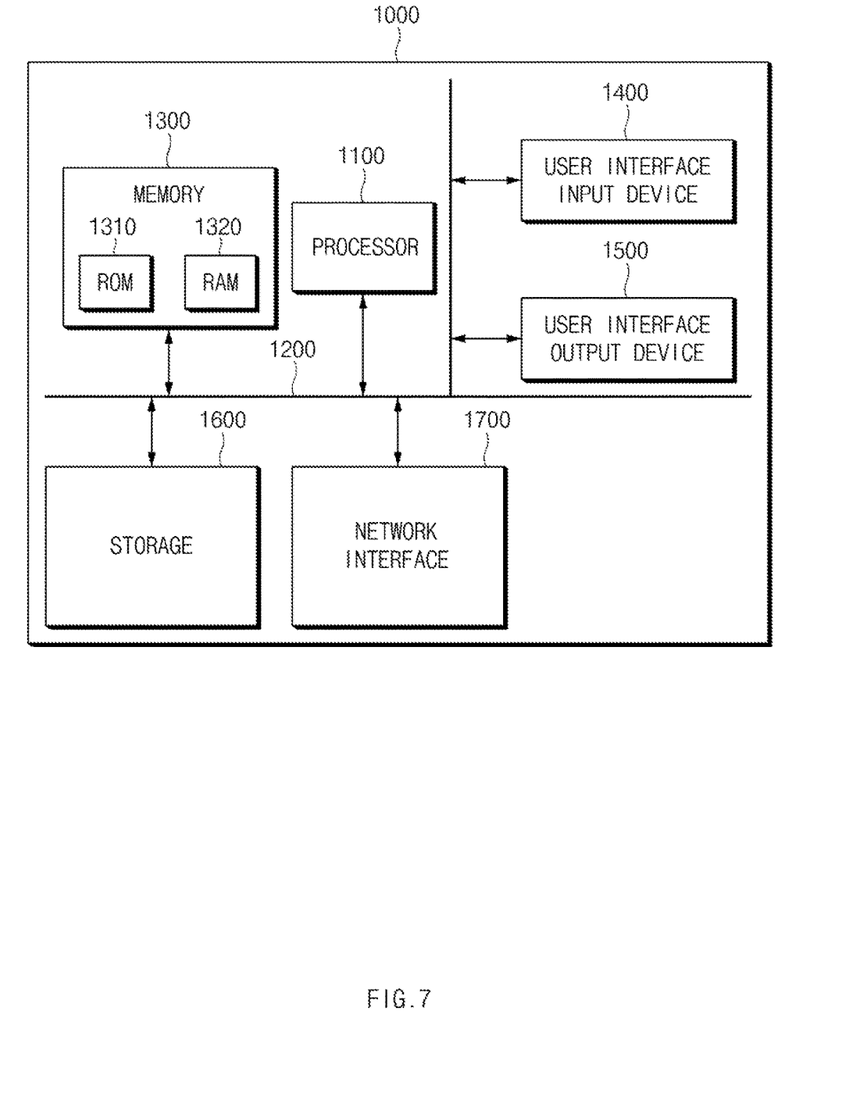
FIG. 7 is a block diagram illustrating a computing system that executes the method according to an form of the present disclosure.

FIG. 7 is a block diagram illustrating a computing system that executes the method in some forms of the present disclosure.

Referring to FIG. 7, the computing system 1000 may include at least one processor 1100 connected through a bus 1200, a memory 1300, a user interface input device 1400, a user interface output device 1500, a storage 1600, and a network interface 1700.

The processor 1100 may be a central processing unit (CPU) or a semiconductor device that processes instructions stored in the memory 1300 and/or the storage 1600. The memory 1300 and the storage 1600 may include various volatile or nonvolatile storage media. For example, the memory 1300 may include a read only memory (ROM) and a random access memory (RAM).

Accordingly, the steps of the method or algorithm described in relation to the forms of the present disclosure may be implemented directly by hardware executed by the processor 1100, a software module, or a combination thereof. The software module may reside in a storage medium (that is, the memory 1300 and/or the storage 1600), such as a RAM memory, a flash memory, a ROM memory, an EPROM memory, an EEPROM memory, a register, a hard disk, a detachable disk, or a CD-ROM. The exemplary storage medium is coupled to the processor 1100, and the processor 1100 may read information from the storage medium and may write information in the storage medium. In another method, the storage medium may be integrated with the processor 1100. The processor and the storage medium may reside in an application specific integrated circuit (ASIC). The ASIC may reside in a user terminal. In another method, the processor and the storage medium may reside in the user terminal as an individual component.

In some forms of the present disclosure, a safety accident maybe prevented in advance by detecting a degree of fatigue of the driver while utilizing biometric information of the driver and actively controlling the vehicle according to an increment of the degree of fatigue.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. An apparatus for controlling a vehicle based on a degree of fatigue of a driver, the apparatus comprising:
   a fatigue degree learning device configured to learn a degree of initial fatigue of the driver based on a heart rate variability (HRV) of the driver received from a sensor after a vehicle ignition is switched on;
   a fatigue degree monitoring device that when learning the degree of initial fatigue of the driver is completed and driving of a vehicle is started, is configured to:
   monitor the degree of current fatigue of the driver based on the HRV of the driver received from the sensor during the driving of the vehicle;
   identify an increment state of the degree of fatigue by comparing the degree of current fatigue of the driver and the degree of initial fatigue of the driver; and
   output a control signal corresponding to the increment state of the degree of fatigue of the driver; and
   a driving controller configured to control the driving of the vehicle based on the control signal,
   wherein the fatigue degree learning device is configured to analyze a first HRV based on a frequency range during a learning period, and learn the degree of initial fatigue of the driver by first log values for a low frequency (LF) and a high frequency (HF) of the first HRV, and
   wherein the fatigue degree monitoring device is configured to analyze a second HRV based on the frequency range during a monitoring period, and detect the degree of current fatigue by second log values for a LF and a HF of the second HRV.

2. The apparatus of claim 1, wherein the fatigue degree learning device is configured to learn the degree of initial fatigue of the driver based on the HRV of the driver received during the learning period for the degree of initial fatigue of the driver.

3. The apparatus of claim 1, wherein the fatigue degree monitoring device is configured to identify the increment of the degree of fatigue of the driver based on reduction ratios of the second log values for the LF and the HF with reference to the first log values for the LF and the HF.

4. The apparatus of claim 3, wherein the fatigue degree monitoring device is configured to:
   output a first control signal corresponding to a first degree of fatigue when it is identified that the second log values for the LF and the HF decrease by not less than a first reference value and less than a second reference value; and
   output a second control signal corresponding to a second degree of fatigue when it is identified that the second log values for the LF and the HF decrease by not less than the second reference value.

5. The apparatus of claim 4, wherein the driving controller is configured to output a warning alarm based on the first control signal.

6. The apparatus of claim 4, wherein the driving controller is configured to control a vehicle-to-vehicle distance of the vehicle based on the second control signal.

7. The apparatus of claim 6, wherein the driving controller is configured to interrupt a data of an accelerator position sensor of the vehicle from being transferred to a throttle valve when a distance between the vehicle and a preceding vehicle is less than a preset distance.

8. The apparatus of claim 4, wherein the driving controller is configured to activate a lane departure warning system (LDWS) and a lane keeping assist system (LKAS) based on the second control signal.

9. The apparatus of claim 1, wherein the driving controller is configured to check a setting of a smart cruise control (SCC) system of the vehicle when the fatigue degree monitoring device outputs the control signal.

10. The apparatus of claim 9, wherein the driving controller is configured to:
control the driving of the vehicle based on the control signal when the SCC system is set to be off; and
output a warning alarm based on the control signal when the SCC system is set to be on.

11. The apparatus of claim 1, wherein the biometric information comprises at least one of an electrocardiogram (ECG), an electroencephalogram (EEG), or an electromyograph (EMG).

12. A method for controlling a vehicle based on a degree of fatigue of a driver, the method comprising:
learning a degree of initial fatigue of the driver based on a heart rate variability (HRV) of the driver received from a sensor after a vehicle ignition is switched on;
when learning the degree of initial fatigue of the driver is completed, monitoring the degree of current fatigue of the driver based on the HRV of the driver received from the sensor during driving of the vehicle;
identifying an increment state of the degree of fatigue by comparing the degree of current fatigue of the driver and the degree of initial fatigue of the driver;
outputting a control signal corresponding to the increment state of the degree of fatigue of the driver; and
controlling the driving of the vehicle based on the control signal,
wherein learning the degree of initial fatigue of the driver comprises:
analyzing a first HRV based on a frequency range during a learning period; and
learning the degree of initial fatigue of the driver by first log values for a low frequency (LF) and a high frequency (HF) of the first HRV, and wherein monitoring the degree of current fatigue of the driver comprises:
analyzing a second HRV based on the frequency range during a monitoring period; and
detecting the degree of current fatigue by second log values for a LF and a HF of the second HRV.

13. The method of claim 12, wherein identifying the increment state of the degree of fatigue comprises:
identifying the increment of the degree of fatigue of the driver based on reduction ratios of the second log values with reference to the first log values.

14. The method of claim 13, wherein outputting the control signal comprises:
when it is identified that the second log values for the LF and the HF decrease by not less than a first reference value and less than a second reference value, outputting a first control signal by determining that the degree of fatigue reaches a first degree of fatigue; and
when it is identified that the second log values for the LF and the HF decrease by not less than a second reference value, outputting a second control signal by determining that the degree of fatigue reaches a second degree of fatigue.

15. The method of claim 14, wherein the control of the driving of the vehicle comprises:
outputting a warning alarm based on the first control signal.

16. The method of claim 14, wherein the control of the driving of the vehicle comprises:
controlling a vehicle-to-vehicle distance of the vehicle based on the second control signal; and
activating a lane departure warning system (LDWS) and a lane keeping assist system (LKAS) of the vehicle.

17. The method of claim 12, wherein the control of the driving of the vehicle comprises:
checking a setting of a smart cruise control (SCC) system of the vehicle;
when the SCC system is set to be off, controlling the driving of the vehicle based on the control signal; and
when the SCC system is set to be on, outputting a warning alarm based on the control signal.

* * * * *